US 6,656,176 B2

(12) United States Patent
Hess et al.

(10) Patent No.: US 6,656,176 B2
(45) Date of Patent: *Dec. 2, 2003

(54) VESSEL HARVESTING RETRACTOR WITH INTEGRAL ELECTROSURGICAL CLAMPING ELEMENTS

(75) Inventors: Christopher J. Hess, Lebanon, OH (US); Michael F. Clem, Maineville, OH (US); Gary W. Knight, West Chester, OH (US); Rudolph H. Nobis, Mason, OH (US); Dale R. Schulze, Lebanon, OH (US)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/967,201

(22) Filed: Sep. 28, 2001

(65) Prior Publication Data

US 2003/0065348 A1 Apr. 3, 2003

(51) Int. Cl.[7] ............................................... A61B 17/32
(52) U.S. Cl. ..................... 606/51; 606/159; 606/206; 606/170; 600/104
(58) Field of Search ............................ 606/170, 190, 606/205, 206, 46, 48–51; 600/104

(56) References Cited

U.S. PATENT DOCUMENTS

| 3,175,556 A | * | 3/1965 | Wood et al. |
| 5,542,949 A | * | 8/1996 | Yoon .................. 606/143 |
| 5,591,183 A | | 1/1997 | Chin |
| 5,593,418 A | | 1/1997 | Mollenauer |
| 5,601,581 A | | 2/1997 | Fogarty et al. |
| 5,667,480 A | | 9/1997 | Knight et al. |
| 5,695,514 A | | 12/1997 | Chin |
| 5,722,934 A | | 3/1998 | Knight et al. |
| 5,725,479 A | | 3/1998 | Knight et al. |
| 5,730,748 A | | 3/1998 | Fogarty et al. |
| 5,797,947 A | | 8/1998 | Mollenauer |
| 5,817,013 A | | 10/1998 | Ginn et al. |
| 5,836,945 A | | 11/1998 | Perkins |
| 5,853,417 A | | 12/1998 | Fogarty et al. |
| RE36,043 E | | 1/1999 | Knighton |
| 5,873,889 A | | 2/1999 | Chin |
| 5,876,413 A | | 3/1999 | Fogarty et al. |
| 5,891,140 A | | 4/1999 | Ginn et al. |
| 5,899,913 A | | 5/1999 | Fogarty et al. |
| 5,902,316 A | | 5/1999 | Mollenauer |
| 5,916,233 A | | 6/1999 | Chin |

(List continued on next page.)

FOREIGN PATENT DOCUMENTS

| EP | 0 979 635 A2 | 2/2000 |
| WO | WO 99/66842 | 12/1999 |
| WO | WO 00/15116 | 3/2000 |

OTHER PUBLICATIONS

PCT Int'l. Search Report, dated Dec. 12, 2002, for PCT Int'l. Appln. No. PCT/US02/30434.

*Primary Examiner*—Michael H. Thaler

(57) ABSTRACT

An endoscopic vessel harvesting device and a method of endoscopic harvesting of vessels from a patients body. The method comprises locating the vessel, and inserting the vessel harvesting device through an incision. Dissecting the vessel from the surrounding tissue, and capturing side branch vessels in a vessel capturing device. Ligating and transecting the side branch vessels using electrodes and a knife located in the vessel capturing device. Finally, ligating and transecting the vessel, and removing the vessel from the patients body. The vessel harvesting device comprises a head piece, a shaft having a lumen for receiving an endoscope, and a vessel capturing device located on the head piece for capturing the side branch vessels in the receiver.

15 Claims, 7 Drawing Sheets

U.S. PATENT DOCUMENTS

| | | |
|---|---|---|
| 5,922,004 A | 7/1999 | DuBois |
| 5,928,135 A | 7/1999 | Knight et al. |
| 5,938,680 A | 8/1999 | Ginn |
| 5,968,065 A | 10/1999 | Chin |
| 5,968,066 A | 10/1999 | Fogarty et al. |
| 5,970,982 A | 10/1999 | Perkins |
| 5,972,010 A | 10/1999 | Taheri |
| 5,976,168 A | 11/1999 | Chin |
| 5,980,549 A | 11/1999 | Chin |
| 5,984,937 A | 11/1999 | Morse et al. |
| 6,019,771 A | 2/2000 | Bennett et al. |
| 6,022,313 A | 2/2000 | Ginn et al. |
| 6,036,713 A | 3/2000 | Kieturakis |
| 6,036,714 A | 3/2000 | Chin |
| 6,042,538 A | 3/2000 | Puskas |
| 6,059,802 A | 5/2000 | Ginn |
| 6,068,639 A | 5/2000 | Fogarty et al. |
| 6,071,232 A | 6/2000 | Knighton et al. |
| 6,120,434 A | 9/2000 | Kimura et al. |
| 6,139,489 A | 10/2000 | Wampler et al. |

* cited by examiner

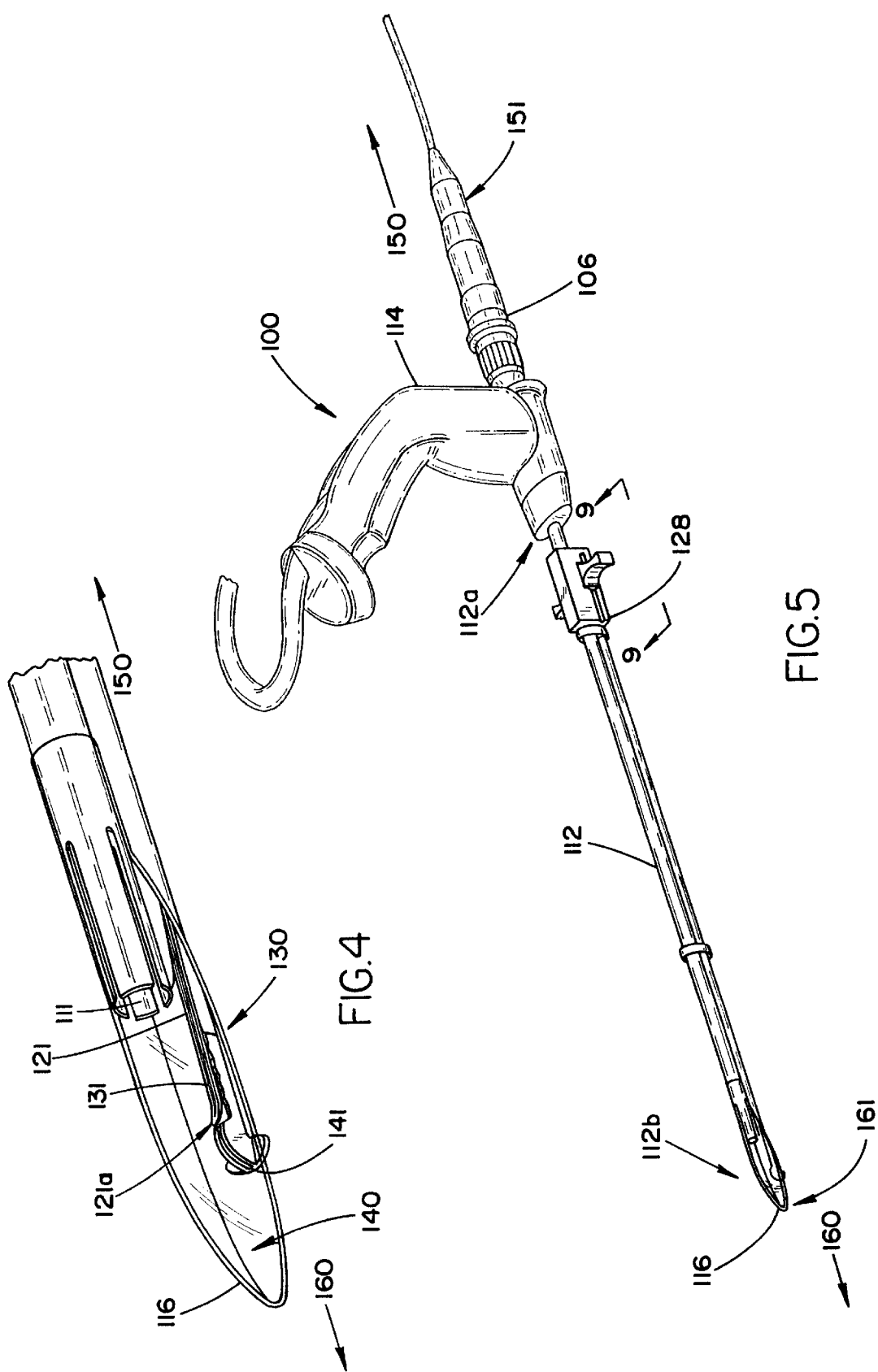

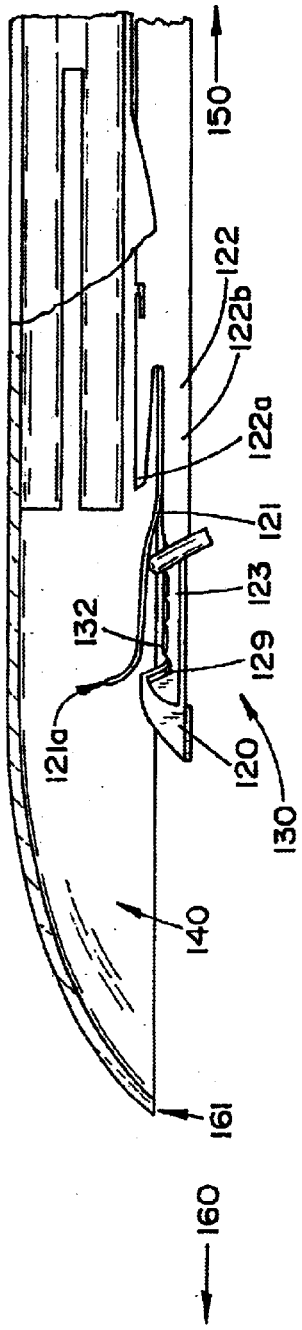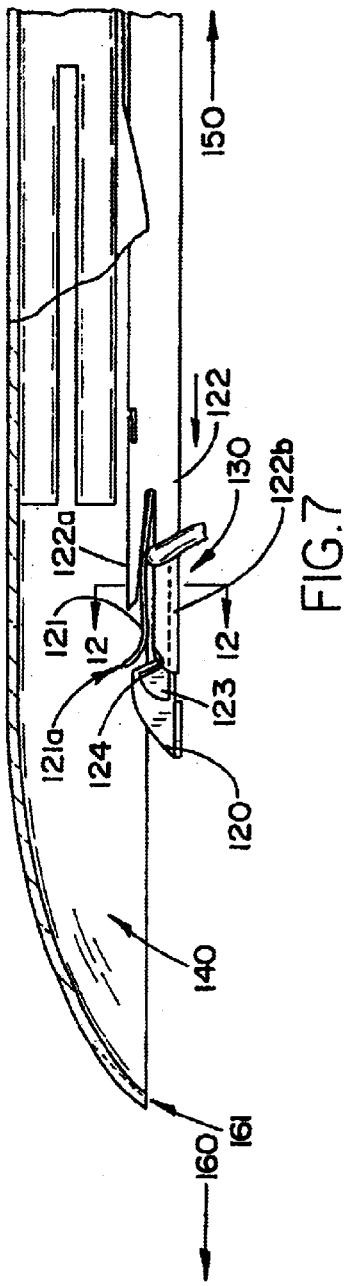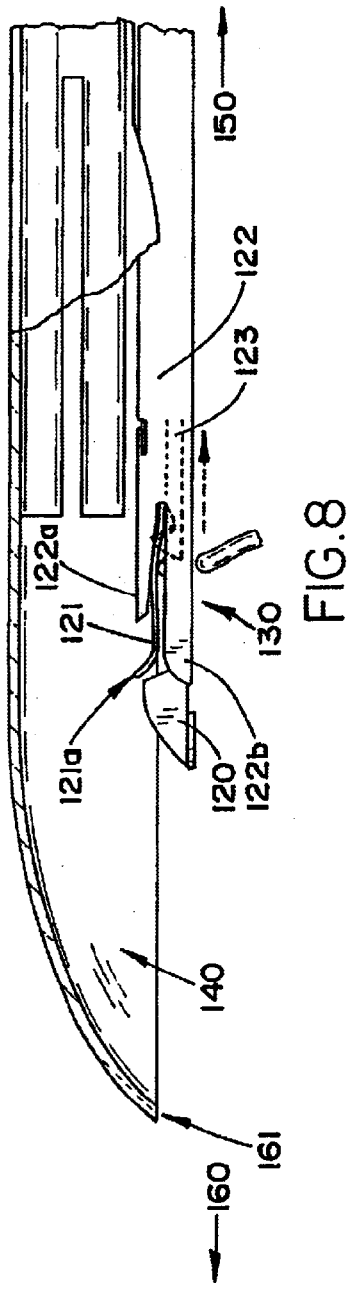

VESSEL HARVESTING RETRACTOR WITH INTEGRAL ELECTROSURGICAL CLAMPING ELEMENTS

FIELD OF THE INVENTION

The present invention relates generally to vessel harvesting and in particular to an improvement over existing endoscopic vessel harvesting techniques and devices.

BACKGROUND OF THE INVENTION

Endoscopic harvesting of vessels is well known in the surgical field and has been the subject of a great deal of recent technological advancement. Typically, the harvesting of vessels is performed so that the vessels can then be used for procedures such as Cardio Artery Bypass Grafting (CABG). In this procedure the saphenous veins of the legs are harvested for subsequent use in the CABG surgery.

Devices and methods for such vessel harvesting are well known and have been described in numerous publications including U.S. Pat. No. 5,667,480 issued Sep. 16, 1997 and U.S. Pat. No. 5,722,934 issued Mar. 3, 1998 to Knight et al, both of which are incorporated herein by their reference. The devices and methods of these patents are briefly described below and are shown in FIGS. 1 and 2.

In the traditional harvesting devices as shown in FIG. 1, there is provided a hollow shaft 12 connected to a concave head piece 16 located at the distal end of the shaft which provides a workspace 18. An endoscope 5 with a distal end 6 is typically inserted in the shaft so that the surgeon may view workspace. The edge of the head piece 17 is used for dissecting the vessel from the surrounding tissue as shown in FIG. 2. The device may also have guide rails located on the underside of the device which allow for the entry of other devices such as dissectors, ligation tools, and cutting tools into the workspace.

The traditional method for removal of a vessel section as shown in FIG. 2 is as follows. Initially an incision 3 is made and the vessel 7 is located. Then, the vessel 7 is dissected from the surrounding tissue using the leading edge of the head piece 16 of the device 10 to separate the tissue from the vessel 7. At this time there is sufficient workspace 18 created around the vessel 7 so that other instruments can be inserted into the incision 3 via the guide rails located on the underside of the device. These instruments include ligation tools for securing side branch vessels, a vessel dissector for performing a more complete dissection of the vessel which is to be removed, and laproscopic scissors for the transection of both the side branch vessels 9 and the vessel 9 which is to be removed.

Of the known devices and methods for removal of vessels there remains one constant problem. The problem is that to perform each an every one of the side branch ligation and transactions, extra tools must be inserted along the guide rails of the device through the original incision. Often times this means that to perform a single transection of a side branch vessel three tools must be inserted in succession into the body. The various tools include, a dissector to dissect the side branch from the surrounding tissue, a ligation tool to clamp the side branch vessel and the vessel to be removed, and a cutting tool to perform the transection. Additionally, the harvesting device remains in the body throughout the procedure.

This requirement of inserting the tools in succession and exchanging one tool for another to perform each step of the operation requires extra time, this in turn can be a drain on the individual surgeons resources. Further, because of this increased amount of time, which the surgeon requires to perform the operation, the stress on the patient is increased. Minimization of patient stress is naturally a concern during any surgical procedure. Therefore, the elimination of some or all of the time extending tool exchanges would greatly benefit not only the patient but the surgeon as well.

SUMMARY OF THE INVENTION

The present invention is directed to solving the shortcomings of known vessel harvesting devices, by providing a superior vessel harvesting device, promoting efficient removal of vessels, and limiting the stress on patients. The objects of the present invention are the minimization of the tool exchanges, increased efficiency of operation, minimization of patient stress, and increased ease of the overall harvest operation. The present invention pertains to a device having a means for capturing side branch vessels so that they may be ligated and transected. The present invention provides for in a single instrument the features that traditionally required at least two and often more instruments. Currently, these several instruments are introduced through the same incision, and held together with the endoscopic portions approximately parallel. This is often referred to as "sword fighting" due to the complications associated with performing the procedure. "Sword fighting" often traumatizes the incision and the internal tissue structures. The effect of requiring two hands to perform the procedure coupled with fact that operators may include both surgeons and surgical assistants of varying skill highlights the advantages of developing a single device to perform these varied tasks. Thus, a single instrument combining the functions of dissection, retraction, visualization of a vessel within a workspace, and division of the vessel, would greatly benefit both the patient and the operator.

Accordingly, a vessel harvesting device is provided. The vessel harvesting device comprises a shaft having a lumen for accepting an endoscope therethrough, a t head piece connected to the distal end of the shaft. The headpiece creates a workspace which can be viewed through an endoscope that is inserted through the shaft. A vessel capturing means, operable within the workspace between an open and a closed position to capture side branch vessels. The vessel capturing means is preferably comprised of a flexible upper jaw and a rigid lower jaw. The device preferably has a handle which is connected to the proximal end of the hollow shaft. The handle allows the operator to manipulate the device.

The vessel capturing means can be opened and closed at the discretion of the operator via an actuating means. Preferably, the vessel capturing means is opened when a tube which surrounds the flexible and rigid portions of the jaw and is retracted towards the proximal end of the device. To close the vessel capturing means, the tube is slid towards the distal end of the device. Upon the dissection of a side branch vessel the operator opens the vessel capturing means allowing the operator to place the side branch vessel inside of the vessel capturing means, effectively capturing the side branch vessel. Upon capture of the side branch vessel, the vessel capturing means is closed.

The vessel capturing means can be fitted with ligation and transection means. This allows the operator to capture, ligate, and transect a side branch vessel without requiring of other instruments to be inserted into the workspace. The transection means is preferably a knife edge housed in the lower jaw. The knife edge is drawn towards the proximal end of the device by an actuation means to cut a side branch vessel.

The ligation means is preferably a bi-polar electrode arrangement wherein the tube, which closes the jaws, is used as one electrode and a raised portion of the cutting means is the other electrode. Upon capture of a side branch vessel in the movable jaw, the side branch vessel is ligated by energizing the electrodes with RF energy.

Also provided is a method of removing a vessel utilizing the above-described device. The first step in such a method involves locating the vessel to be removed. Next an incision is made in the patient to expose the vessel and the harvesting device is inserted through the incision in the usual manner. The head of the device is used to dissect the vessel to be removed from the surrounding tissue. Upon dissection, side branch vessels are exposed. The vessel harvesting means, located on the distal end of the device is then placed over the side branch vessel. The side branch vessels are then captured, the vessel capturing means is closed and the side branch vessel is held in place by the now closed vessel capturing means. The side branch vessels are then ligated and transected by the ligation and transection means which are located in the vessel capturing means. The ligation means is preferably a pair of bi-polar electrodes which are energized with RF energy upon capture of the side branch vessels. The ligation means is preferably a knife housed in a lower jaw of the vessel capturing means. The knife transects the ligated side branch vessel upon being drawn in the proximal direction by the user via the actuating means.

This use of the vessel capturing means and the ligation and transection means located therein limits the number of tools which must be inserted into the incision. Further, by having the ligation and transection means located in the vessel capturing means, the procedure is more easily performed, and with a minimum of stress to the patient and in a decreased amount of time.

BRIEF SUMMARY OF THE DRAWINGS

FIG. 4 illustrates a perspective view of the head piece of a preferred implementation of an endoscopic vessel harvesting device of the present invention.

FIG. 5 illustrates a perspective view of a preferred implementation of the endoscopic vessel harvesting device of the present invention.

FIG. 6 illustrates an enlarged side view of the head piece of the endoscopic harvesting device of FIG. 4 in which the vessel capturing means is open and the vessel has been inserted.

FIG. 7 illustrates an enlarged side view of the head piece of the endoscopic harvesting device of FIG. 6 in which the vessel capturing means is closed around the vessel.

FIG. 8 illustrates an enlarged side view of a head piece for the endoscopic harvesting device of FIG. 7 in which a knife cuts the vessel.

DESCRIPTION OF THE PREFERRED EMBODIMENTS

Figure 1:
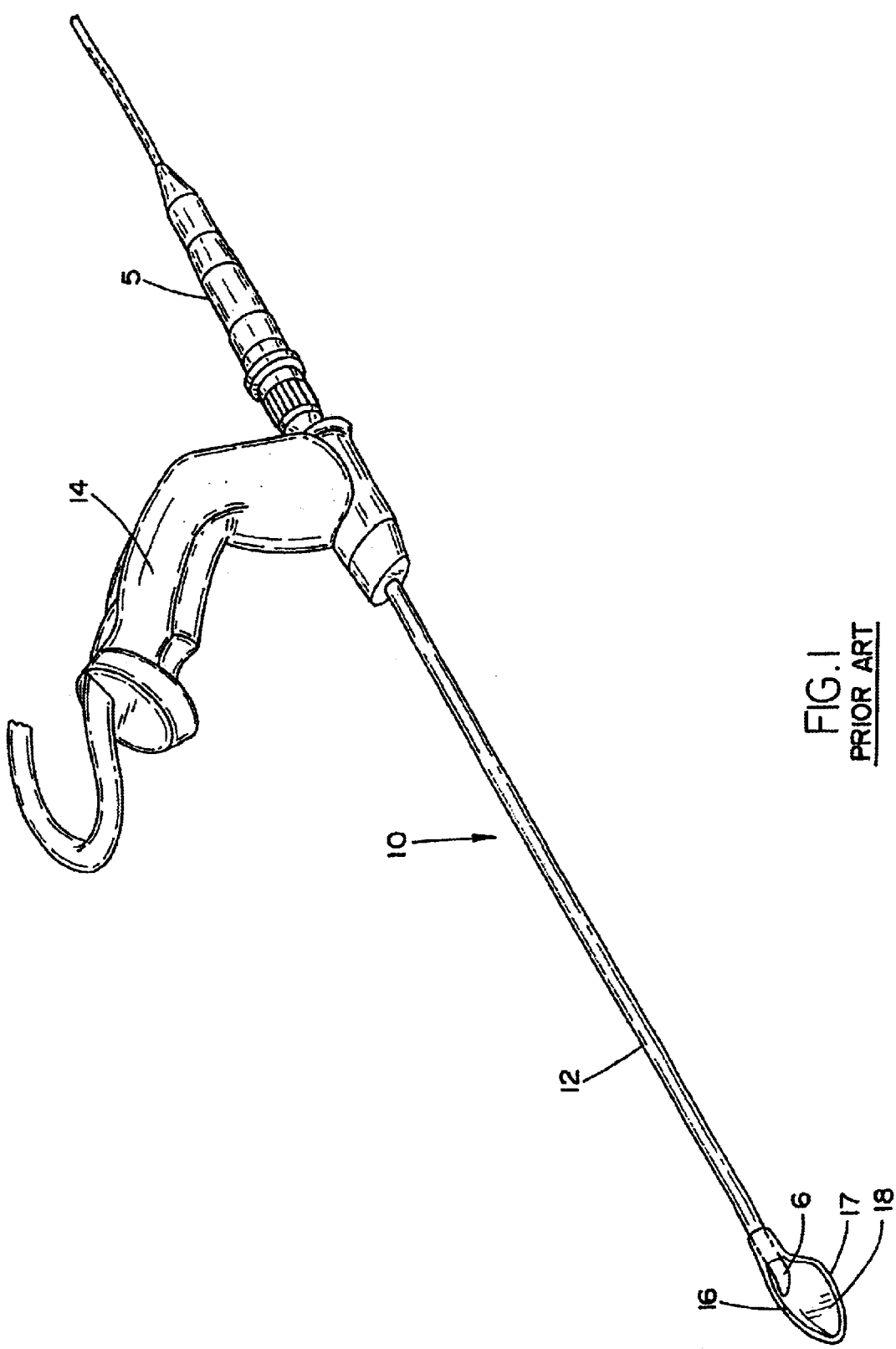
FIG. 1 illustrates a perspective view of an endoscopic vessel harvesting device of the prior art.

Referring now to FIGS. 4 and 5, a preferred implementation of an endoscopic vessel harvesting device (EVH) for the removal of vessels from a body is illustrated therein, generally referred to by reference number 100. Specifically, the EVH 100 is often used for the removal of the saphenous vein from the leg of a patient undergoing a CABG operation. The embodiments discussed herein are directed to the removal of such a saphenous veins, however, it should be noted that they are not limited to the removal of saphenous veins and could be utilized for the removal of any vessel from a patient. As described above, traditionally the procedure of removing the saphenous vein required the exchange of various tools multiple times for each side branch ligation and transection.

Accordingly, the EVH 100 is provided to overcome the disadvantages of the prior art. The vessel harvesting device (EVH) 100 comprises a shaft 112 having a lumen 111 therethrough for the insertion of an endoscope 106. The shaft is preferably formed of a rigid material, for example a medical grade stainless steel, or a rigid plastic. At the proximal end 112a of the shaft is a handle 114, formed preferably of a thermoplastic. At the distal end 112b of the shaft is a head piece 116. The head piece 116 is preferably fabricated of a substantially transparent medical grade material such as polycarbonate.

Referring now to FIGS. 6–8, on the underside of the device and projecting into the area defined by the head piece 116, often called a workspace 140, is a vessel capturing means 130. The vessel capturing means 130 is designed to not interfere with the dissection process or with observation of the dissection through the endoscope 106. During the dissection, the head piece 116 operates as is known in the art such as that described in U.S. Pat. Nos. 5,667,480, and 5,722,934, both of which are incorporated herein by their reference. The preferred vessel capturing means 130 comprises a lower jaw 120, an upper jaw 121, a tube 122 for closing the vessel capturing means, a cutting means 123, and a knife edge 129, as shown in FIGS. 6, 7 and 8.

The lower jaw 120 is comprised of rigid material that resists movement and operates as a foundation for the other components. The rigid material is preferably formed of a polycarbonate plastic. The upper jaw 121 is formed of flexible material and it is preferably this portion of the vessel capturing means 130 that moves between the open and closed positions. The flexible material is preferably also a polycarbonate plastic but formed with a smaller thickness than the upper jaw. The flexible upper jaw 121 has a low profile to limit interference with the head piece 116. When in the open or original position the upper jaw 121 is upwardly biased, preferably by the spring tension of the flexible material. When in the closed position the flexible upper jaw 121 is compressed against the lower jaw 120. The flexible upper jaw 121 is preferably shaped so that the distal end 121a of the flexible jaw 121 projects upwardly towards the head piece 116. This upturned distal end 121a of the upper flexible jaw 121 assists in the capture of the vessels. The upper flexible jaw is preferably accommodated with a gap 131 which allows for the passage of a transection means through the flexible upper jaw 121. The upper and lower jaws 120, 121 may optionally be molded as a single piece.

Figure 12:
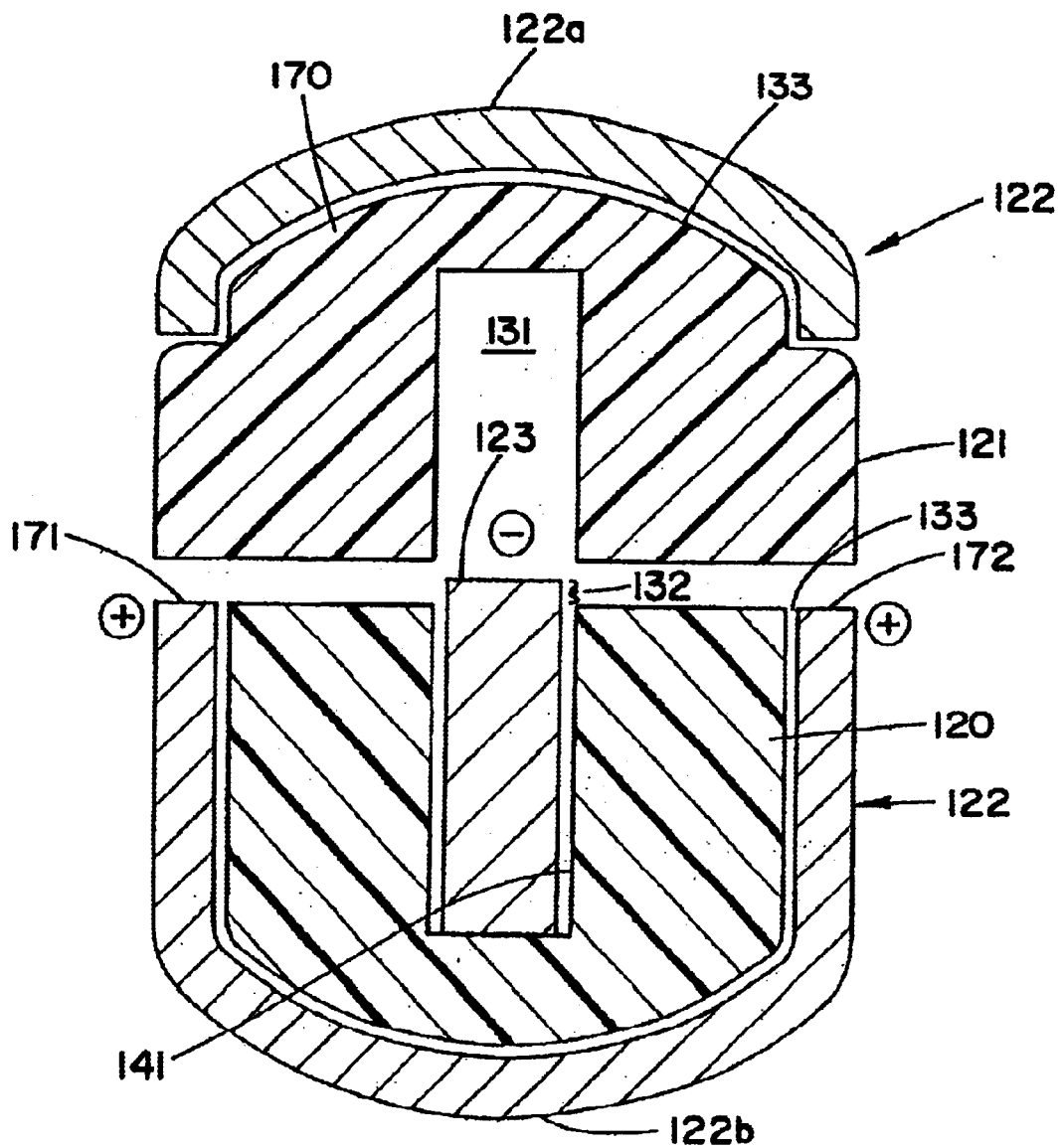
FIG. 12 illustrates a cross sectional view of the capturing means in which the capturing means is closed taken along line 12—12 of FIG. 7.

As shown in FIGS. 4 and 12 the vessel capturing means 130 is preferably equipped with a transection means such as knife edge 129 of cutting means 123 slidingly housed a slot 141 in the lower jaw 120. The knife edge 129 is preferably formed of a medical grade heat treated stainless steel, wherein at least the knife edge 129 is hardened to maintain its sharpness throughout the life of the EVH 100. Preferably, the knife edge 129 is formed on only one side of the cutting means 123, and cuts in one direction. The cutting means 123 is actuated, by an actuation means 127 located in an actuation means housing 128 on the proximal end 112a of shaft 112. While the knife edge 129 is stored in the lower jaw 120, a raised portion 132 of the cutting means 123 protrudes vertically above the level of the lower jaw 120, as can be seen in FIG. 12. The cutting means 123 is preferably formed of a conductive material such as a medical grade stainless steel. The cutting means 123 is electrically connected to an RF energy generating source (not shown) and is coated with an electrically insulating material such as parylene-n except for the raised portion 132 which contacts tissue. The cutting means 123 is slidably housed in a slot 141 in the lower jaw 120. A portion of the lower jaw 120 prevents the knife edge 129 from being exposed when the knife edge 129 is in the stored position, as shown in FIG. 7. The gap 131 in the upper jaw 121 facilitates the cutting of captured vessels by allowing the cutting means 123 and knife edge 129 to be actuated in the proximal direction 150, without interference of the upper jaw 121. Upon a movement in the proximal direction 150 the knife edge 129 extends vertically through the gap 131 and above the level of the upper jaw 121, the knife edge 129 transecting a captured vessel.

The tube 122 is formed of a conductive material, for example a medical grade stainless steel, and is connected to an actuating means 125. Tube 122 is formed of an upper arm 122A and a lower arm 122. The upper and lower arms 122A,B are separated from one another so that when tube 122 is moved in the distal direction 160 a vessel captured between the upper and lower jaws 120, 121 can be accommodated between the upper and lower arms 122A,B so that only a left edge 171 and a right edge 172 of the tube 122 directly contact the vessel. Left and right edges 171, 172 are electrically active and have the opposite polarity of raised portion 132 of cutting means 123. Attached to the inside of upper arm 122A of tube 122 is a spacer 133 as show in FIG. 12, which moves along with the tube 122. The spacer is preferably made of medical grade plastic and can be attached to the tube using glue or other affixing means known in the art. The spacer assists in flattening the upper jaw 121 against the lower law 120, when the vessel capturing means 130 is closed.

The actuating means 125 comprises preferably at least one control knob 126, 127 connected to the tube 122, which allows the user to move the tube in both the distal 160 and proximal 150 directions relative to the upper and lower jaws 121, 120. The tube 122, when moved towards the distal end 161 of the EVH 100, surrounds the upper and lower jaws 121,120 and forces the flexible upper jaw 121 in the direction of the rigid lower jaw 120, effectively closing the vessel capturing means 130. The tube 122 is of small enough diameter that upon closure the upper 121 and lower 120 jaws are compressed together. To open the vessel capturing 130 means the tube 122 is moved in the proximal direction 150. This releases the pressure on the upper flexible jaw 121, and the spring tension of the flexible material of the upper flexible jaw 121 causes the vessel capturing means 130 to resume its original shape. The vessel capturing means 130 does not "open" like traditional jawed devices but returns to its original shape. This is advantageous over other known devices as the profile of the device is smaller and the upper jaw 121 does not interfere with the headpiece 116 when the vessel capturing means 130 is in the original or opened position.

Figure 9:
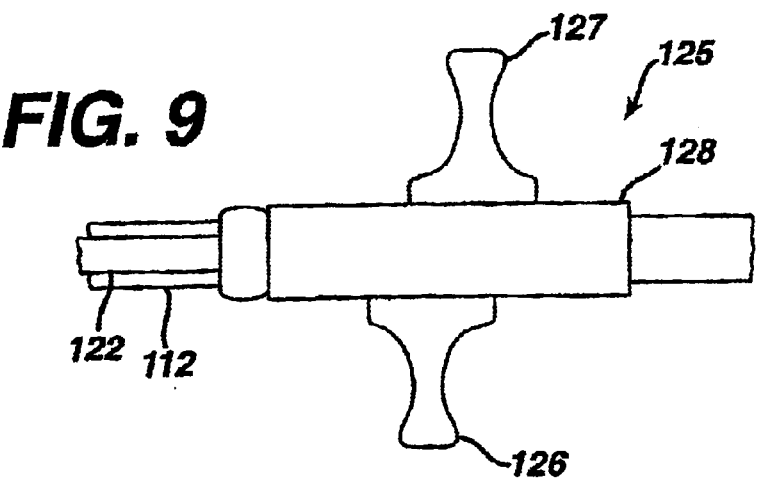
FIG. 9 illustrates a top view of the actuating means, positioned such that the knife is housed in the lower jaw and the capturing means is open.
Figure 10:
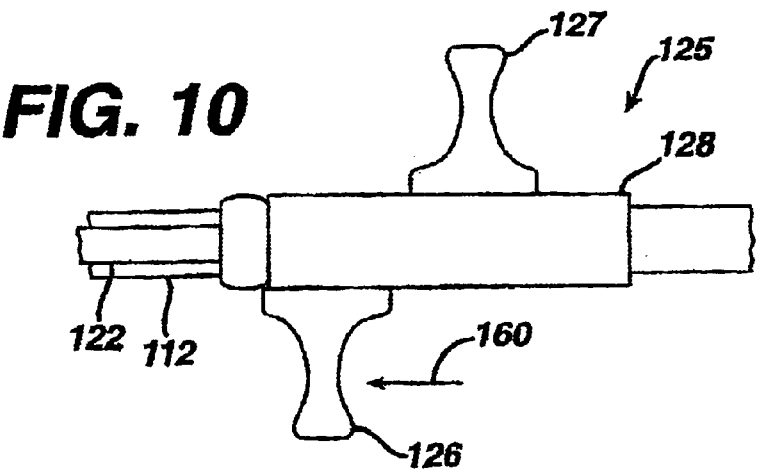
FIG. 10 illustrates a top view of the actuating means positioned such that the knife is housed in the lower jaw and the capturing means is closed.
Figure 11:
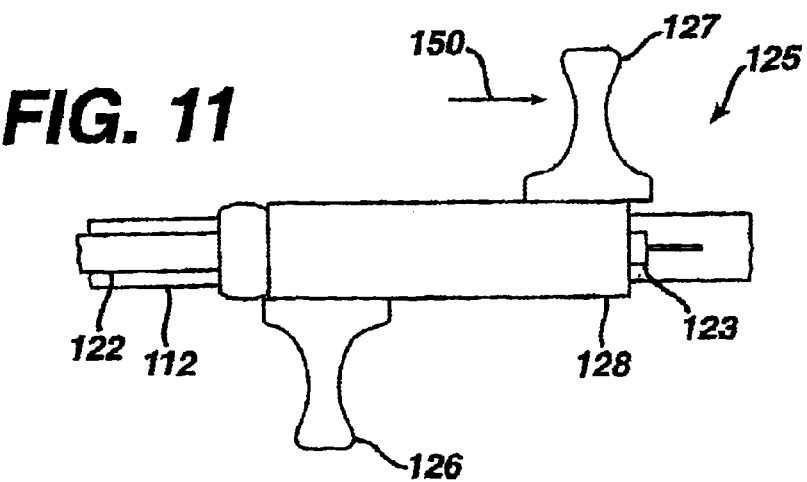
FIG. 11 illustrates a top view of the actuating means positioned such that the knife has been actuated and the capturing means is closed.

The actuation means 125 preferably comprises at least one control knob 126, 127, one of which is connected to the tube 122 for closing the movable jaw 130 and the other is connected to the cutting means 123. The actuation means 125 includes a housing 128 into which the proximal end of the tube 122 is inserted. A control knob 126 connects to the tube 122 through the actuation means housing 128. One of the control knobs 126, 127 acts on the proximal end of the tube 122 and manipulates the tube 122 as a control rod. Similarly, control knob 127 connects to a control rod (not shown) connected to the cutting means 123 via the actuation means housing 128. A control rod (not shown) for the cutting means 123 connects the control knob 127 to the cutting means 123 and preferably runs through a lumen 133 of the tube 122. The cutting means 123 and the tube 122 move independently of one another and both move in a one to one fashion with the control knobs 126, 127 respectively. It is the movement of the control knobs 126 and 127, as shown in FIGS. 9–11, which causes the movements of the components at the distal end 161 of the EVH 100, as shown in FIGS. 6–8. The movements of the components of the EVH 100 in FIGS. 6–8 and 9–11 correspond to one another, respectively.

In FIGS. 6 and 9, the vessel capturing means 130 is opened by the operator, by moving a control knob 126 towards the proximal end of the EVH 100. The control knob 126 is connected to tube 122 and a proximal movement thereof results in a corresponding proximal movement of the tube 122. This is usually done upon the exposure of a side branch vessel which needs to be ligated and transected during the harvesting procedure. The opening of the vessel capturing means 130 by moving control knob 126 towards the proximal end 151 of the EVH 100 allows the side branch to be placed under the biased flexible upper jaw 121 as shown in FIG. 6. Preferably, this is performed by opening the vessel capturing means 130, and moving the EVH 100 in the direction of the exposed vessel so that the vessel enters the vessel capturing means 130. The vessel is positioned under the opened flexible upper jaw 121 and on top of the rigid lower jaw 120. Upon entry of the vessel into the vessel capturing means 130, the capturing means 130 can be closed by sliding the tube 122 in the distal direction 160.

As shown in FIGS. 7 and 10, closing of the vessel capturing means 130 results in the vessel being captured by the EVH 100. This is performed by moving control knob 126 distally which results in a corresponding movement in the distal direction 160 of the tube 122 connected thereto. The tube 122 encircles the flexible upper jaw 121 and rigid lower jaw 120 and forces the vessel capturing means 130 to close. With the vessel in this location the vessel can be ligated and transected.

As shown in FIGS. 8 and 11, upon closing of the vessel capturing means 130, the captured vessel is compressed between the flexible upper jaw 121 and the rigid lower jaw 120. One of the features of the present invention is that the vessel capturing means 130 is preferably fit with a ligation, and transection means. The ligation means is preferably at least two electrodes which can be energized with RF energy. A preferable electrode configuration is shown in FIG. 12, where one electrode is preferably the tube 122, which closes the vessel capturing means 130, the second electrode is preferably the raised portion 132 of the cutting means 123 which is preferably raised above the surface level of the lower jaw 120. Alternatively the portion of the cutting means 123 can be level with the lower jaw 120, or recessed below the lower jaw 120. Additionally, the cutting means 123 is coated with an insulative material such as parylene-n except on the raised area 132 which contacts the vessel. The respective electrodes are connected to an RF energy generator as is known in the art. Upon closing of the vessel capturing means 130, the compression of the upper jaw against the lower jaw preferably causes any fluid in the vessel to be forced laterally away from the area being compressed. This reduces the spread of vaporizing fluids from the sides of the vessel capturing means 130, thus limiting the thermal injury to the vessel and surrounding tissue when the electrodes are energized with RF energy. In an alternate embodiment, knife edge 129 of the cutting means 123 is not coated with an electrically insulative material. This allows the complete sharpening of the knife edge 129 after the coating process is completed. A trade off with this alternate embodiment, however, is that un-insulated, knife edge 129 can contacted tissue while RF energy is being applied therefore, the current density on the knife edge 129 could be higher than desired and the quality of the coagulation could be compromised. The cutting means 123 is preferably actuated by moving control knob 127 in a proximal direction 150, which results in a corresponding proximal movement of the cutting means 123 operatively connected thereto. This movement transects a captured and ligated side branch vessel.

This cutting of the side branch vessels without the use of extraneous tools results in a more efficient procedure which causes less trauma to the patient. Further, the minimization of tool exchanges, created by the combination of several features into a single instrument simplifies the procedure making it more applicable to a wider range of potential users.

Figure 2:
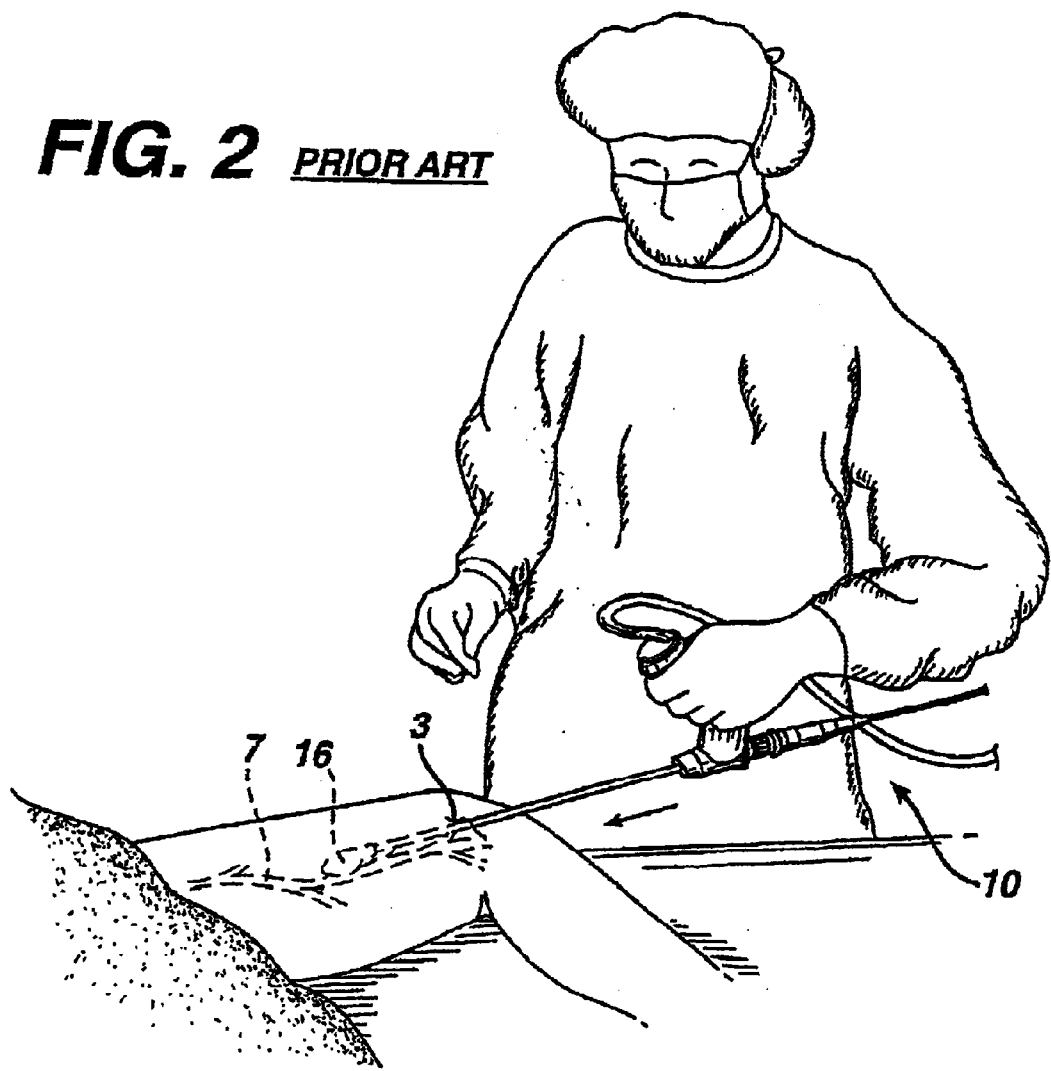
FIG. 2 illustrates a perspective view of a surgeon and an endoscopic vessel harvesting device of the prior art harvesting a vein located in a persons leg.
Figure 3:
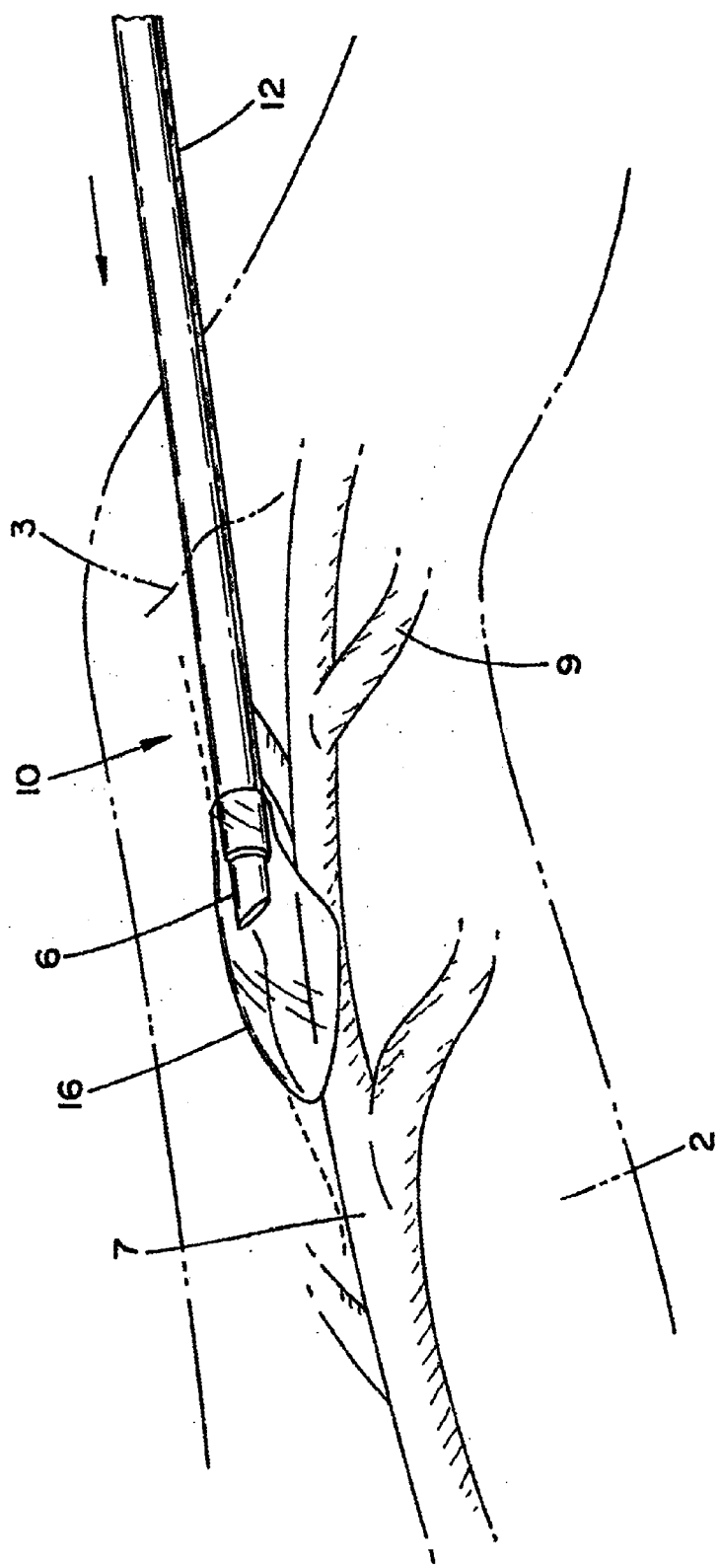
FIG. 3 illustrates an enlarged perspective view of the endoscopic vessel harvesting of FIG. 1 inserted into a patient during a procedure to harvest a vein.

The traditional method for the removal of the saphenous vein is well known in the art and shown in FIGS. 1–3. Initially, an incision 3 is made in the patients leg 2. The incision is typically three or four cm in length and provides access to the vessel 7. The vessel 7 is surrounded by tissue from which it must be dissected. This is accomplished using the edge 17 of the headpiece 16 of the harvesting device 10. This allows the vessel to be accessed by the harvesting device 10 and through the dissection the head provides a workspace 18 to continue the dissection and proceed with removal of the vessel 7. During the dissection process, the operator will uncover numerous side branch vessels which are attached to the saphenous vein. Typically, 10 to 15 side branches are uncovered in a procedure to remove 18 inches of saphenous vein from the upper and lower leg. Each of these side branch vessels must be individually dissected, ligated and transected so that the saphenous vein may be removed.

A method of removing the saphenous vein using the EVH 100 as described above will now be discussed with reference to the Figures. Those skilled in the art will appreciate that the methods of the present invention limit the number of extraneous tools which must be inserted into the same incision.

The method includes the steps of locating the vessel to be removed making an incision, and inserting the EVH 100 into the incision. The blunt dissection of the vessel is performed by moving the head piece 116 of the EVH 100 along the vessel. This separates the vessel from tissue above the vessel and exposes the vessel to the EVH 100. Separation of the vessel from tissue beneath the vessel is performed using the tip and sides of the head piece 116. The operator moves the handle from side to side and longitudinally in a reciprocating fashion to continue dissecting the vessel. Once the vessel is exposed, and separated from the surrounding tissue, a workspace 140 is defined by the head piece 116. The workspace provides a location for the attached vessel capturing means 130 to be operated.

The vessel will undoubtedly have a number of side branch vessels connected to it. Each of these will have to be individually ligated and transected before removal of the vessel. Upon the exposing of a side branch vessel the headpiece 116 can be placed over the side branch vessel with the upper flexible jaw 121 in the opened position. With the flexible upper jaw 121 opened, the side branch vessel is positioned under the flexible upper jaw 121 and on the rigid lower jaw 120 by manipulation of the handle 114 of the endoscopic vessel harvesting device. The entry of the side branch is facilitated by the upturned distal end 121a of the flexible upper jaw 121. Upon entry of the side branch vessel into the vessel capturing means 130, the flexible upper jaw 121 is closed by the surgeon by moving the tube 122 towards the distal end 161 of the EVH 100.

The captured vessel is then compressed by the closing of the vessel capturing means 130. The side branch vessel is sandwiched between opposing sides of the flexible upper jaw 121 and rigid lower jaw 120.

The vessel capturing means 130 may also be fitted with transection and ligation means. These means are actuated by the operator using their respective controls. The surgeon can actuate the ligation means, which are preferably a pair of electrodes, by energizing the electrodes 122 and 123 with RF energy via a switch (not shown) located in the handle 114 of the EVH 100 or by using a foot pedal (not shown) as is common in the art. With the vessel capturing means 130 closed and the side branch vessel between the upper flexible jaw 121 and lower rigid jaw 120 RF energy can be supplied to the electrodes, one of which is preferably the tube 122 used to close the jaw and the second electrode is preferably a raised portion 132 of the cutting means 123, this effectively ligates or cauterizes the side branch vessel.

After the side branch vessel is ligated it can be transected. The side branch vessel can be transected using a knife edge 129 located on cutting means 123 which is housed in the rigid lower jaw 120. This knife edge 129 is actuated by manipulating control knob 127 on actuating means 125 towards the proximal end of the device 151. Upon transection of the side branch vessel the surgeon can proceed with the dissection of the vessel and move to the next side branch vessel requiring ligation and transection.

Those skilled in the art will appreciate that the methods of the present invention do not require the insertion of any extraneous tools to perform the transection and ligation procedure. Nor do they require multiple tool exchanges. Accordingly, the procedure as a whole is far easier, and efficient that those previously known. As a result the stress on the patient is reduced.

Although only a few exemplary embodiments of this invention have been described in detail above, those skilled in the art will readily appreciate that many modifications are possible without materially departing from the novel teachings and advantages of this invention. Accordingly, all such modification are intended to be included within the scope of this invention as defined in the following claims.

What is claimed is:

1. A vessel harvesting device comprising:
a shaft having a lumen for acceptance of an endoscope therein;
a head piece connected to a distal end of the shaft, the head piece defining a workspace;
a vessel capturing means, operable within the workspace between an open and a closed position to capture a vessel therein, said vessel capturing means comprising:
a lower jaw;
a flexible upper jaw; and
a closing means for compressing the vessel between the flexible upper jaw and the lower jaw;
a handle connected to a proximate end of the shaft, for allowing the operator to manipulate the head piece; and
a first actuation means located between the handle and the distal end of the shaft, for operating the closing means.

2. The vessel harvesting device as claimed in claim 1, wherein said closing means is a tube including upper and lower arms which surround the flexible upper jaw and the lower jaw forcing the flexible upper jaw and the lower jaw into compressed alignment upon a movement of the tube towards the distal end of the device, wherein the vessel is compressed between the upper and lower jaws.

3. The vessel harvesting device as claimed in claim 1, wherein a distal tip of the flexible upper jaw is curled away from the lower jaw to facilitate positioning of flexible upper and lower jaws around the vessel.

4. The vessel harvesting device as claimed in claim 1, wherein the vessel capturing means further comprises ligation means and transection means, for ligating and transecting the captured vessel, respectively.

5. The vessel harvesting device as claimed in claim 4, wherein the ligation means comprise a first and second electrode, the first and second electrodes being of different polarities and cooperatively arranged to cauterize the captured vessel of the vessel upon energizing of the electrode with RF energy.

6. The vessel harvesting device as claimed in claim 5, wherein the first electrode comprises the tube and the second electrode is disposed in the lower jaw, and is off-set from any portion of the tube.

7. The vessel harvesting device as claimed in claim 6, further comprising a second actuation means for moving the knife.

8. The vessel harvesting device as claimed in claim 4, wherein the transection means comprises a knife, the knife being housed in the distal end of the lower jaw, the knife cutting a captured vessel upon a movement of the knife towards the proximate end of the device.

9. A method of harvesting vessels comprising:
providing a vessel harvesting device comprising a shaft having a lumen for acceptance of an endoscope therein, a head piece connected to a distal end of the shaft, the head piece defining a workspace, a vessel capturing means comprising a lower jaw, a flexible upper jaw, and a closing means for closing the flexible jaw upon the lower jaw to capture a side branch vessel, the vessel capturing means being operable within the workspace between an open and a closed position to capture a side branch of the vessel, a handle connected to a proximate end of the shaft, for allowing the operator to manipulate the head piece, and an actuation means located between the handle and the distal end of the shaft, for operating the closing means, wherein the closing means is a tube which surrounds both the flexible upper and lower jaws, the tube forcing the flexible upper jaw towards the lower jaw upon a movement of the tube towards the distal end of the device;
locating a vessel to be harvested;
making an incision to expose the vessel;
inserting the vessel harvesting device into the patient through the incision;
dissecting the vessel from the surrounding tissue with the vessel harvesting device;
capturing a side branch of the vessel using the vessel capturing means;
closing the vessel capturing means by sliding the tube over the flexible upper jaw and the lower jaw of the vessel capturing means;
ligating and transecting the side branch of the vessel using the vessel capturing means; and
removing the vessel.

10. The method of harvesting vessels as claimed in claim 9, wherein the ligating of the side branch comprises applying RF energy to the side branch using a first and second electrodes, wherein the first and second electrodes are of different polarity.

11. The method of harvesting vessels as claimed in claim 9, wherein the transecting of the side branch comprises drawing a knife housed in the lower jaw towards the proximate end of the device.

12. The method of harvesting vessels as claimed in claim 9, wherein the capturing comprises opening the upper jaw and forcing the device in the distal direction to allow the side branch vessel to enter between the upper and lower jaws.

13. The method of harvesting vessels as claimed in claim 9, wherein the closing comprises compressing the side branch between a first and second electrode.

14. The method of harvesting vessels as claimed in claim 13, wherein the ligating of the side branch comprises applying RF energy to cauterize the captured side branch vessel.

15. The method of harvesting vessels as claimed in claim 14, wherein transecting of the side branch comprises drawing a knife housed in the lower jaw towards the proximate end of the device subsequent to the ligation of the side branch vessel.

* * * * *